United States Patent [19]

Humphrey et al.

[11] Patent Number: 4,561,738

[45] Date of Patent: Dec. 31, 1985

[54] FIELD TESTER

[75] Inventors: William E. Humphrey, San Leandro; Charles Campbell, Berkeley, both of Calif.

[73] Assignee: Humphrey Instruments, Inc., San Leandro, Calif.

[21] Appl. No.: 436,876

[22] Filed: Oct. 26, 1982

[51] Int. Cl.$^4$ ............................................. A61B 3/02
[52] U.S. Cl. .................................................. 351/226
[58] Field of Search .......................... 351/224, 225, 226

[56] References Cited

U.S. PATENT DOCUMENTS

| 2,441,031 | 5/1948 | Papritz | 351/226 |
|---|---|---|---|
| 3,288,546 | 11/1966 | Gans . | |
| 3,414,348 | 12/1968 | Gambs | 351/225 X |
| 4,045,130 | 8/1977 | Krahn . | |
| 4,260,227 | 4/1981 | Munnerlyn | 351/226 |

OTHER PUBLICATIONS

E. L. Greve, R. W. De Boer and H. Pynappel-Groothuyse, *Perimetron,* Docum. Ophthal. Proc. Series, vol. 22, p. 69.

E. L. Greve, *Peritest,* Docum. Ophthal. Proc. Series, vol. 22, pp. 71–73.

*Primary Examiner*—Rodney B. Bovernick
*Attorney, Agent, or Firm*—Townsend and Townsend

[57] ABSTRACT

A field tester wherein a patient's tested eye is located at the center of an interior hemisphere defining a projection surface and wherein a light spot is projected onto said surface from an eccentric location is disclosed. Optics in common with the projector assure that the off-center projected light is of constant intensity and diameter as selected for each test sequence according to test criteria. Specifically, a filament light source is projected to a collimating lens. The light source is re-imaged to a system lens stop. There is a movable aperture between the collimating lens and the first lens of telescopic optics for projecting the image of the aperture onto the projection surface of the sphere. By using a coordinate transform to predict the distance from the point of light source projection to the projection surface of the sphere, the movable aperture is registered to a conjugate distance with respect to the telescope optics. Aperture registration insures projection of a constant image of the aperture to any point along sphere surface. There results a field testing spot of constant diameter and intensity, according to selected image criteria, in spite of a continuously changing distance between the point of projection and projecting surface on the inside projection hemisphere. An apertured finder for centering of the patient's eye is also disclosed wherein relay optics projecting a real image of the patient's eye as viewed through a peep hole assure a wide angle view of the eye being tested. The eye is viewed through an aperture having a sight that does not significantly interfere with the test being conducted.

17 Claims, 17 Drawing Figures

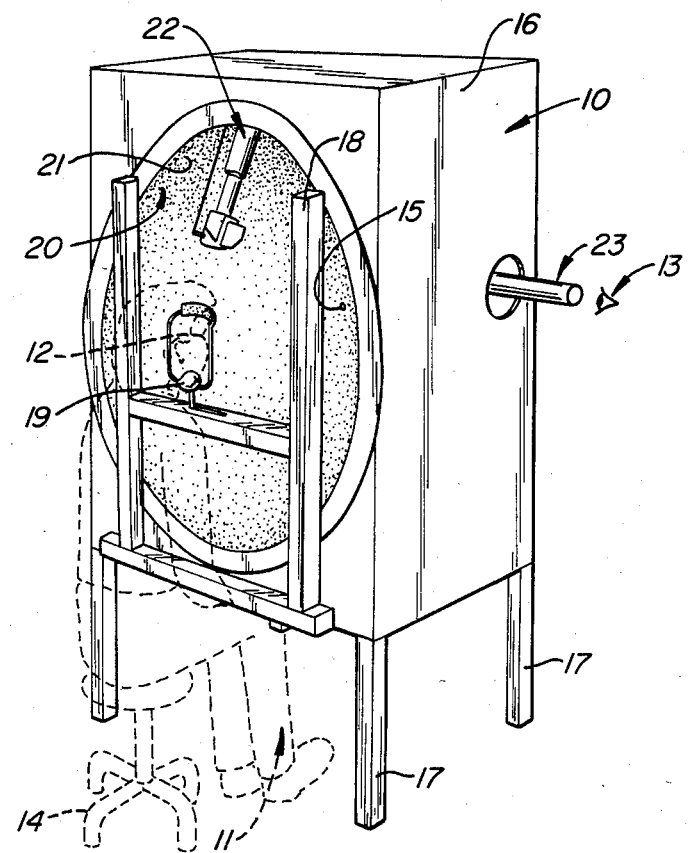
FIG.__1.

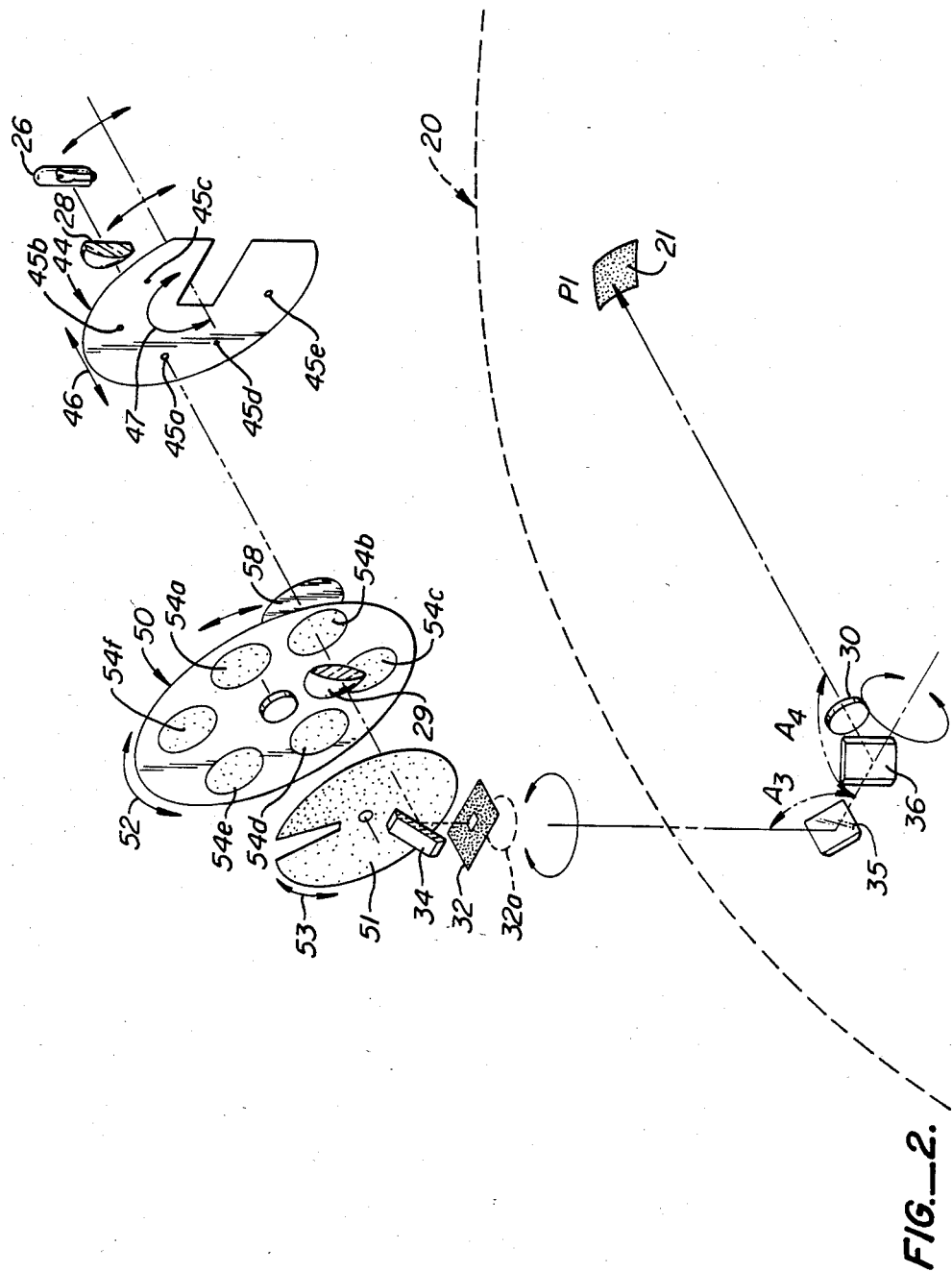
FIG._2.

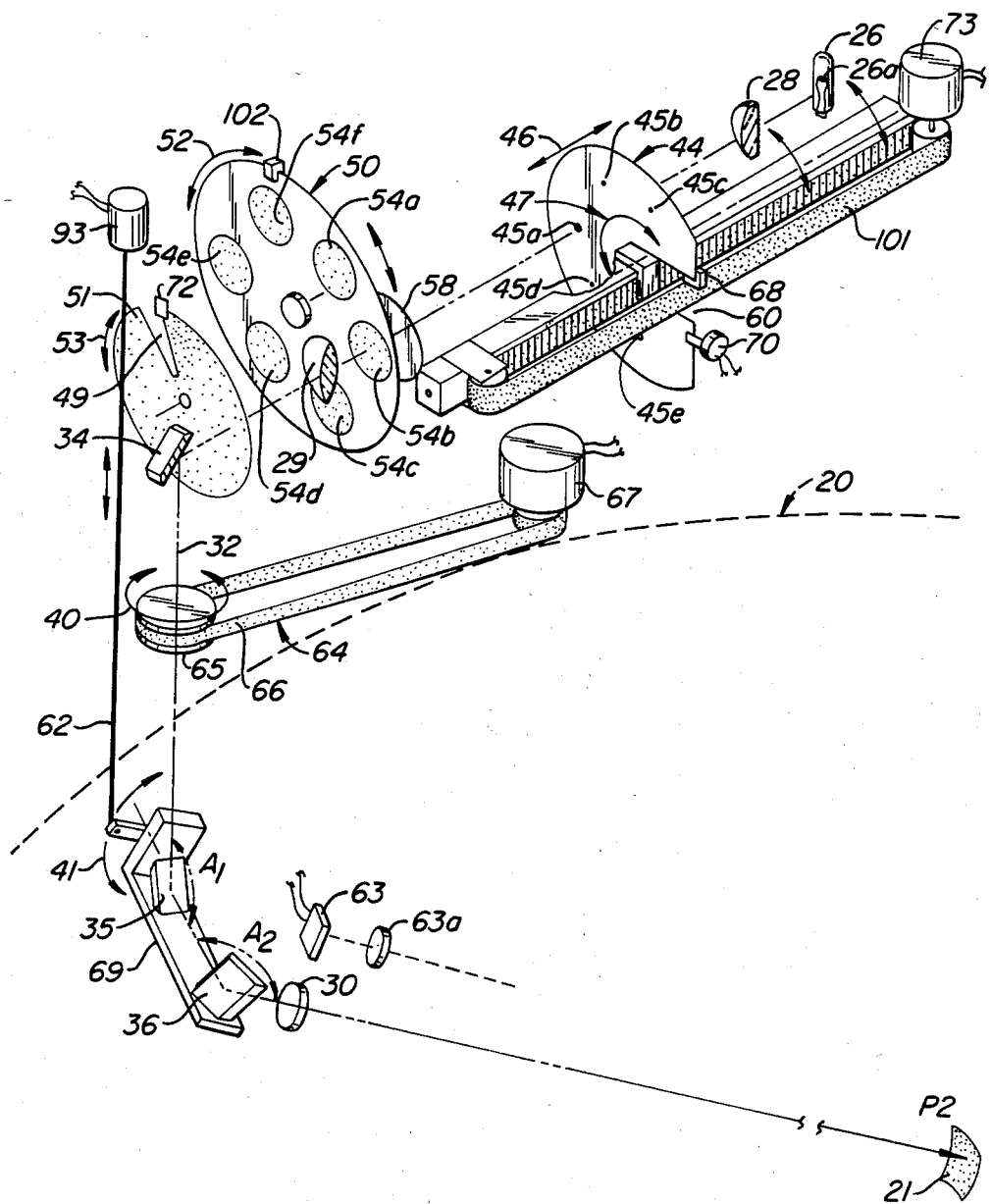
FIG._3.

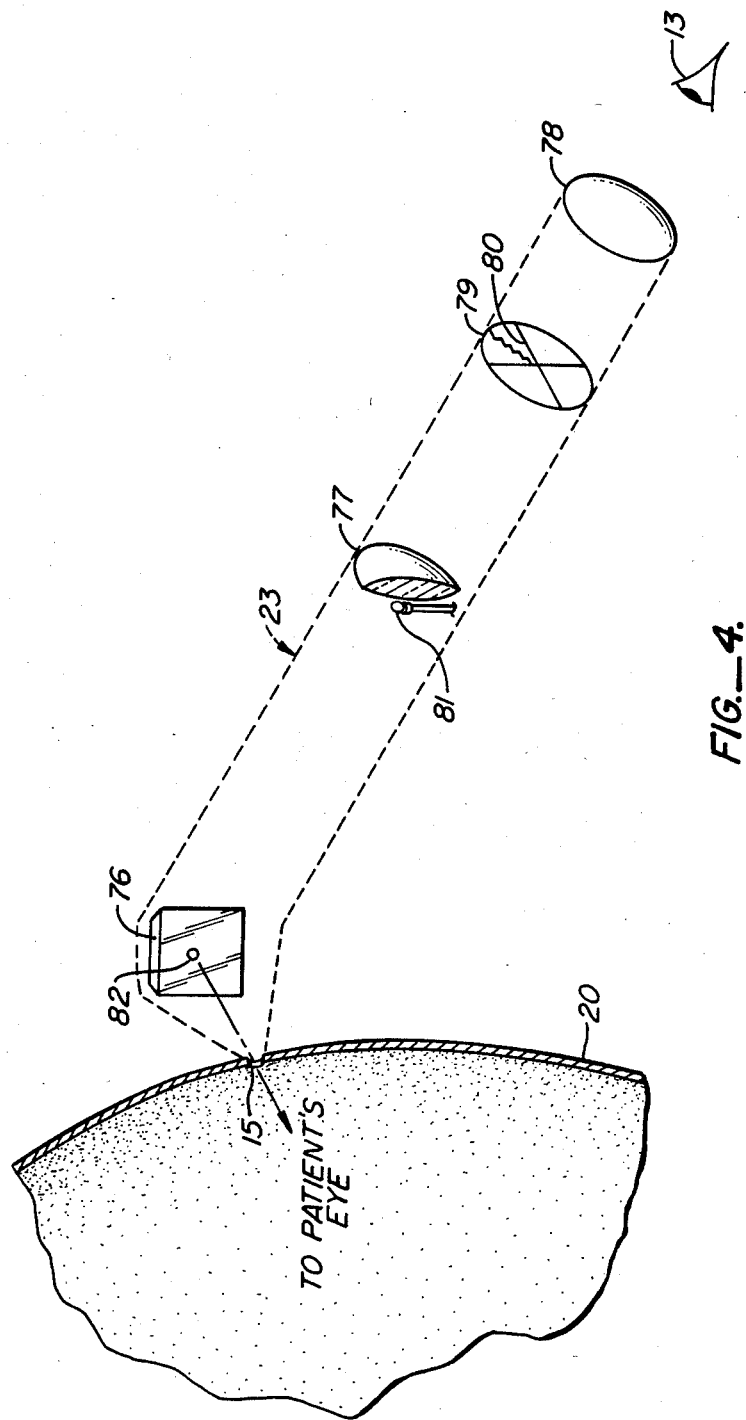
FIG._4.

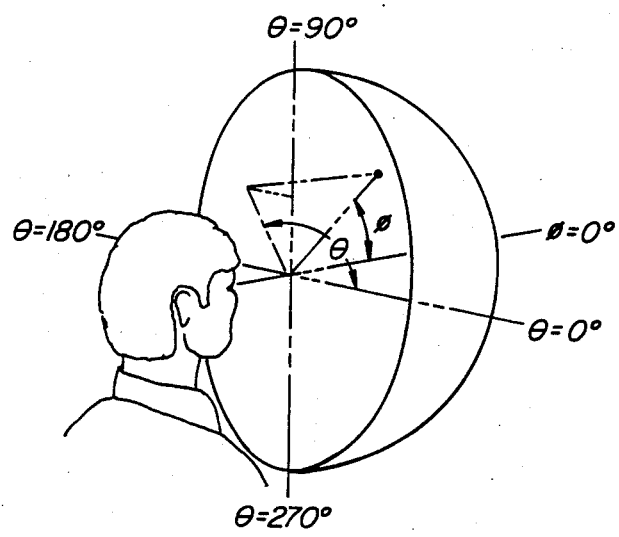
FIG._5A.
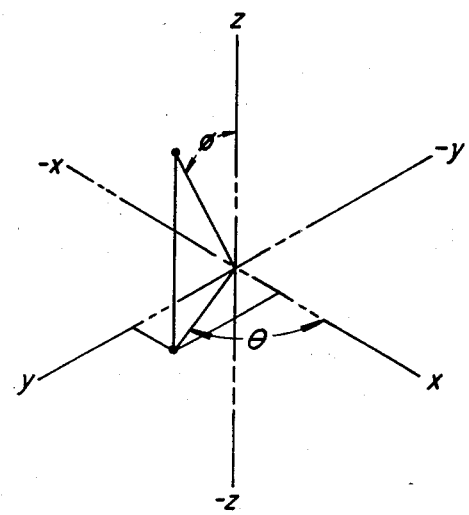
FIG._5B.
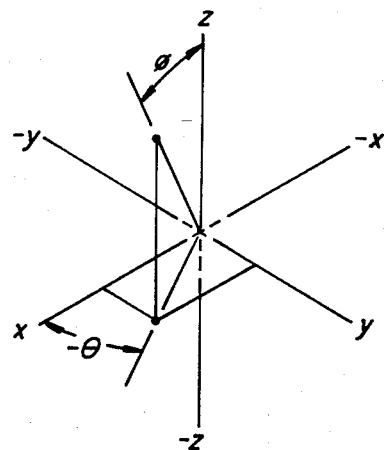
FIG._5C.
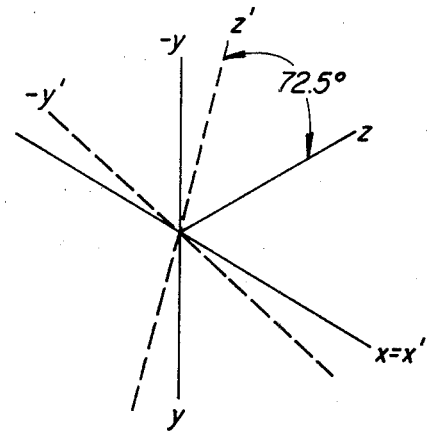
FIG._5D.

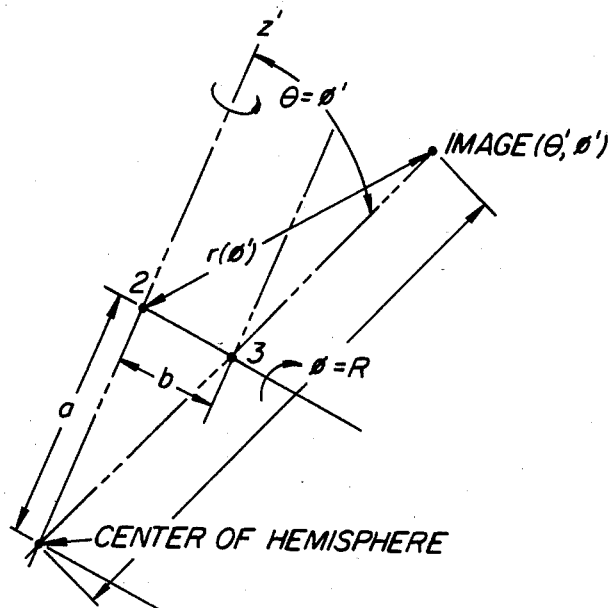
FIG._5E.
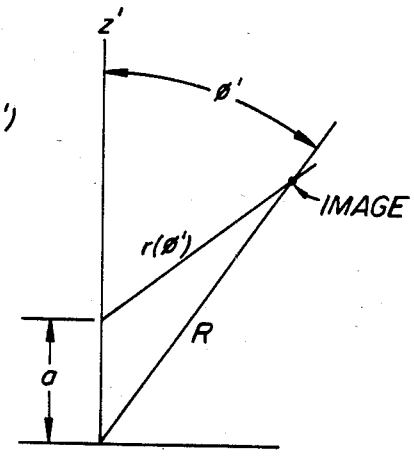
FIG._5F.
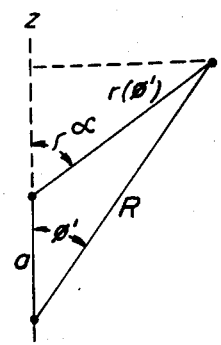
FIG._5H.
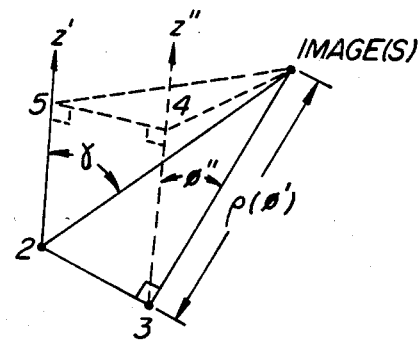
FIG._5G.
FIG._5I.

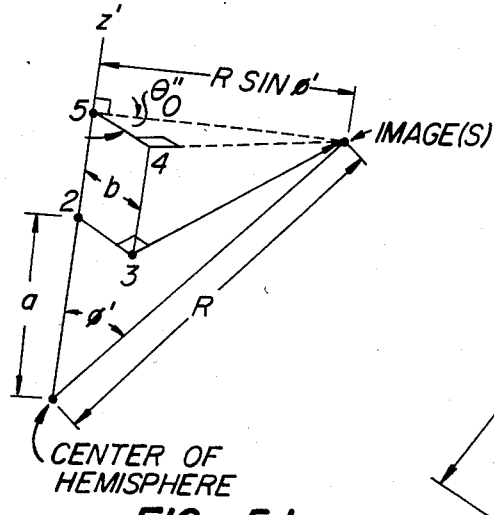
FIG._5J.
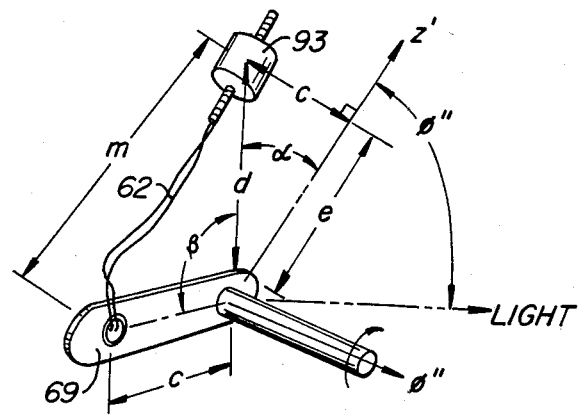
FIG._6A.
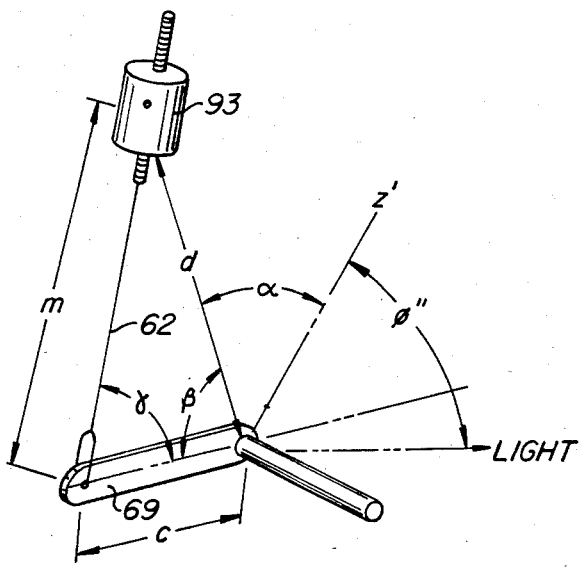
FIG._6B.
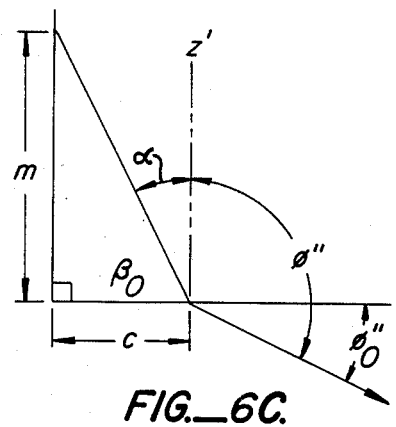
FIG._6C.

FIELD TESTER

BACKGROUND OF THE INVENTION

1. Field of the Invention

This invention relates to field testers. More specifically, this invention includes a field tester of type wherein the inside surface of a projection hemisphere provides for visual field intensity testing with a movable spot of light having examiner selected parameters, such as size, intensity, and brightness, that are maintained constant during a testing sequence in spite of continuously changing focal length and distance from an image projection point.

2. Description of the Prior Art

Field testers are known. It is common to include a hemispheric projection surface and place the tested eye of the patient at the center of the hemisphere. Thereafter, light sources are sequentially flashed on the surface of the hemisphere. After instructing the patient to a central fixation, an examiner notes the ability of the patient to see the sides of the sphere and the light sources flashed. The patient's so called "field" is thereafter recorded and used to plot the absence, presence, and even progress of disease.

These instruments are of several types. In a first type, an array of lights is mounted to penetrate through the surface of the sphere (see for example Gains, U.S. Pat. No. 3,288,546). Such devices are usually limited in the color and intensity of light projected as by the type of light source used. For example, where diodes are used, only monochromatic tests are possible.

In another type of device, light projection is made to coincide as closely as possible to the center of the sphere where the patient's eye and forehead frequently reside. As a consequence, the point of beam projection physically interferes with the point of patient placement. Thus, all the difficulties of off-axis projection are present, including improper focus of a light beam on the inside projection of the dome and variation in intensity of the projected light beam. (See for example Krahn U.S. Pat. No. 4,045,130).

Off-center projection has heretofore been used. Such projection has included scanning the inside surface of the hemisphere with a target path comprising a plurality of semi-closed loops. Generally, the path of the loops has been directed to all points on the inside surface that are equidistant from a projection point. The image is projected in a great circle fashion such that sectors of the inside surface are defined. When one sector has been tested, the projector is moved and another sector is tested. The projector is typically moved in one of two ways: it is swung by a mechanical arm horizontally and transverse of the inside surface in an arc, or it is moved about the periphery of the inside surface. These approaches, although maintaining constant image size and intensity due to the equal distance from the projection point to the inside surface for all points in a sector, are not ideal in a testing environment. The device of the type having a mechanical arm is not suited for automated testing; the arm must swing behind the patient's head during the test, creating a hazard wherein the patient could bump into the swinging area. The device having peripheral projection requires complex rotary movement of its entire optical system. Such an approach unnecessarily complicates the field tester mechanism.

SUMMARY OF THE INVENTION

A field tester wherein a patient's tested eye is located at the center of an interior hemisphere defining a projection surface and wherein a light spot is projected onto said surface from an eccentric location is disclosed. Optics in common with the projector assure that the off-center projected light is maintained at constant intensity and diameter, as determined by examiner selected parameters. Specifically, a filament light source is projected through a collimating lens. The light source is re-imaged to a system lens stop. There is a movable aperture between the collimating lens and telescopic optics for projecting the image of the aperture onto the projection surface of the sphere.

By using a coordinate transform to predict the distance from the point of light source projection to the projection surface of the sphere, the movable aperture is registered to a conjugate distance with respect to the telescope optics. Aperture registration insures projection of a constant image of the aperture to any point along the sphere surface. There results a field testing spot that is maintained at constant diameter and intensity, according to examiner selected criteria, in spite of a continuously changing distance between the point of projection and the projection surface.

An apertured finder for centering of the patient's eye is also disclosed wherein relay optics projecting a real image of the eye assure a wide angle view of the eye being tested. The eye is viewed through an aperture having a sight that does not significantly interfere with the test being conducted.

An object of the invention is to disclose an off-center projection system for a hemispheric projection surface which projection system preserves projected image size and image intensity, as selected according to examiner specified test criteria, in spite of constantly changing distance between the point of projection and the point on the inside surface of the hemisphere where projection occurs. According to this aspect of the invention, a light source is projected through a collimator to the first lens of telescopic optics for projecting an image to the inside and projection surface of the projection hemisphere. An aperture is movable along the path of collimation where it can only receive light of substantially constant intensity even though it is moved varying distances from the light source. By the expedient of moving the aperture to a conjugate distance with respect to the telescopic optics, projection of an image of the aperture to the inside surface of the hemisphere is assured. At the same time, the intensity of the image on the inside surface of the hemisphere remains unchanged, even though the projection distance constantly changes.

An advantage of the disclosed lens train is that it may be conveniently folded by moving mirrors. For example, by a system of two orthogonal pivoted mirrors, the beam may be projected to all surfaces on the inside of the projection hemisphere.

Another advantage of the present invention is that the size of the projected spot remains the same. Specifically, it is a property of the disclosed telescope that as the aperture moves towards the first lens of the telescope, the resultant beam is focused for projection at a further distance. However, the end and resulting size of the spot remains constant.

It is a surprising result of this invention that the projection of the spot varies in projected distance without changing in intensity. According to this aspect of the invention the aperture movable in the collimated light path must by definition always emit the same amount of light. This is true whether the aperture is towards the light source or away from the light source. Since the remaining telescopic optics serve only to relay the image to the conjugate location, the image uses only that light passed by the aperture, the light passed by the aperture being constant because of collimation.

An advantage of the disclosed lens train and constant image projection system is that a white full spectrum source can be used for projection. Moreover, the interposition of neutral density filters and color filters allow for testing of the eye throughout the observable spectrum.

Yet another object of this invention is to disclose a wide angle viewing system for centering of the eye of the patient to be tested in the center of the sphere. According to this aspect of the invention, an insignificant and small hole in the nature of a "peep hole" is placed in the back of the observing hemisphere. A lens is placed behind the hemisphere with the peep hole at a first conjugate location and the eye of the observer at a second conjugate location. A suitable eyepiece is used for viewing the real and projected image of the patient's eye a short distance away from the eye of the observer. There results a wide angle view of the patient's eye being tested in the field tester, which wide angle enables rapid and precise centering.

An advantage of this aspect of the invention is that the interference of the hole with the projection surface on the inside of the hemisphere is insignificant. Additionally, light source projection to the center of the hemisphere along the patient's line of sight can easily be made.

Yet another aspect of this invention is that the peep hole used for eye centering can also be used for a light fixation source of a patient. This light fixation source can either be combined with the centering optical train or alternately can be a small and independent source.

BRIEF DESCRIPTION OF THE DRAWINGS

Other objects, features, and advantages of this invention will become more apparent after referring to the specification, and figures, in which:

FIG. 1 is an over all perspective view of the invention shown from behind and above a patient and illustrating the placement of the patient's right eye at the center of the projection sphere, the off-center projection of the field spot, and the eye only of the examiner in suitable position for observing and centering the eye of the patient within the instrument;

FIG. 2 is an optical schematic shown in three dimensions illustrating the projection of a light beam in substantially the same position as the projection illustrated in FIG. 1;

FIG. 3 is a second schematic of the light projection source of FIG. 2 illustrating the projection of light to a second and greater distance from the projection source and illustrating the movement of the projecting mirror and aperture to assure a focused image of constant intensity at a different distance from the light source; and FIG. 4 is a schematic of the light centering optics of this invention illustrating the projection of the eye of the examiner to and towards the peep hole;

FIGS. 5a–5j show a coordinate system wherein a mathematical model of the present invention is described; and FIGS. 6a–6c show a coordinate system wherein a mathematical model of a stepper motor and bell crank portion of the present invention are described.

DETAILED DESCRIPTION OF A PREFERRED EMBODIMENT

The present invention is a field tester 10 (FIG. 1). In the Fig., a patient 11 is seated on a stool 14 in front of the field tester cabinet 16. The patient rests his chin on a chin rest 19 supported by a patient positioning frame 18. The patient's eyes 12 are aligned through a viewing system 23 by an examiner 13. The patient gazes into the center portion of a hemisphere 20 which includes a projection surface 21. A series of images are formed upon the hemispheric projection surface 21 by a projection system 22.

The purpose of the field tester is to test the patient's field of vision. To this end, a spot of light (the image) is projected at different locations onto the hemispheric surface. If the patient is able to see the projected image, he so indicates it to the examiner. The examiner notes the location of those images seen by the patient and thus can create a field of vision map. The field of vision test results may also be determined by a calculating device (not shown).

The projection system 22 in the present invention provides off-center projection of an image onto the hemispheric surface 21 while maintaining constant light intensity and spot (image) size during the test, in accordance with the test parameters chosen by the examiner. The off-center arrangement of the projection system prevents interference by the projection system with the location of the patient's head within the field tester. It is essential that the projected image be maintained at its selected size and brillance during each test sequence such that an accurate measurement of the patient's field of vision is obtained. For example, an image of varying intensity or size may or may not elicit a response from the patient when a particular portion of the field of vision is being tested. Such a result may not have been obtained had the image been of a constant size or intensity. Thus, an error is produced, making the diagnosing of progressive diseases of the eye much more difficult.

The projection system 22 comprises a light source 26 (FIG. 2) for illuminating the image to be formed. The light source may be any light source such as a halogen incandescent lamp, as manufactured by General Electric Company of Syracuse, N.Y.

Light emanating from the light source 26 is collimated by condenser element 28. The collimated light behaves in such a manner that the light rays are in parallel alignment and the light striking an object is always of constant intensity.

Within the optical path or axis between condenser element 28 and lens 29 is an aperture member such as disc 44 that includes a plurality of various sized apertures 45a–45e. Light striking the aperture disc 44 passes through an aperture near the optical axis (aperture 45a in the example of FIG. 2). The light passing through the aperture thereafter may be used to project an image of a light dot onto the hemispheric projection surface.

The light passing through aperture 45a is intercepted by a shutter 58. The shutter allows light to pass during a testing interval and prevents the passage of light during relocation of the image, prior to or at the conclusion of a test.

After being passed by the shutter, light may be passed through a filter wheel 50 including filters of various colors 54*a*–54*f*. By selecting appropriate filters, the response of a patient's eye to various light wavelengths may be determined. After passing through the filter wheel, light passes through lens 29.

Lens 29 is the first lens in a constant magnification telescope system for projecting the image onto the hemispheric surface. The image striking lens 29 is focused at a focal point within an optical train including lens 29, mirrors 34–36, and lens 30. Interposed within the optical train is a variable neutral density filter 51 for varying the intensity of light that passes through the optical train. Additionally, there is an optical stop 32 in the optical train for preventing interference due to reflection and spurious images. The stop is smaller in size than light source filament 26*a* so that movement of the filament does not result in variation in light density within the image projected onto the projection surface.

The optical train is folded by means of mirrors 34–36. The image may be projected on any part of the hemisphere 20 projection surface 21 depending on the positioning of mirrors 35 and 36.

Referring now to FIG. 3, a system of servos and detectors is shown. Apertured disc 44 is shown having a slot 60 which is positioned proximate to an edge detector 70. The edge detector indicates the presence of the wheel slot and thus serves as an initialization position for disc 44. The edge detector 70 produces a signal which is provided to a drive (not shown) by which disc 44 may be rotated about an axis as shown at 47. Rotation of the apertured disc allows the examiner to position a selected aperture 45*a*–45*e* within the light path in between light source 26 and the above-mentioned optical train. In this way, images of various selected sizes may be projected onto the hemispheric projection surface in accordance with the requirements of each patient being tested.

The aperture disc assembly 44 has an additional edge detector 68 that senses the presence of the disc along the linear path between the light source and collimator 28, and lens 29. Movement along this path is indicated by line 46 in FIG. 3. Motion of the disc along this path is accomplished by a drive, such as stepper motor 73 and associated linkage 101. It will be appreciated that although edge detectors and stepper motors are shown, positioning of the apertured objective can be just as readily accomplished by mechanical (as opposed to electromechanical) means or it could be manually positioned.

The projection system, which includes the telescopic optics 29/30, allows an image to be formed at any position along the hemispheric surface 21. To this end, a linkage arm 62 is connected to a linear stepper motor 93, which is provided for rotating the projection path (lens 30) from the optic train about a first axis as indicated by 41. A drive means 64, comprising stepper motor 67, belt 66, and pulley 65, is provided for rotating the projection path of the optic train about a second axis, as indicated by 40.

Shutter 58 may be operated by conventional drive means (not shown). Additionally, filter wheel 50 and neutral density filter 51 may be rotated as indicated by 52 and 53, respectively. Such rotation allows selection of varying color filters 54*a*–54*f* and varying degrees of optical density. Rotation of the filter wheel and neutral density filter is accomplished by a motor or other such drive means (not shown). Additionally, neutral density filter 51 includes slot 49 and an associated edge detector 72 for sensing filter positioning; filter wheel 50 position is also tracked by an edge detector 102.

In one embodiment of the invention the neutral density filter may be coupled to a photocell 63 and associated lens 63*a*. The photocell monitors the background intensity of the projection surface 21 as well as the intensity of the projected image itself. Background intensity may be that of the ambient or a background light source may be provided.

The photocell, in conjunction with the neutral density filter 51 and edge detector 72, may act as a light intensity fine tuning servo. In other embodiments of the invention, the photocell operates a light source brightness control (not shown).

In operation, the size of the projected image and intensity of the projected image are maintained as a constant. As the image is projected to different points on the hemispheric surface 21, mirrors 35/36 are rotated about two axes 40/41. The mirrors are mounted to a projection base, such as bell crank assembly 69 and as such, the relationship between the mirrors is predictable.

FIG. 2 shows projection of an image 21 to point P1 on hemispheric surface 21. To effect such projection, the angle of light reflected from mirror 35 ($A_3$) to mirror 36 and from mirror 36 through lens 30 ($A_4$) onto surface 21 is adjusted by positioning of the mirrors about axes 40 and 41 respectively. Because the distance from the point of projection at lens 30 to the hemispheric surface 21 varies from point P1 to P2 (FIG. 3), the size and intensity of the image formed on a hemispheric surface would normally vary as focus of the image changes with distance. Such variation in intensity and image size tends to invalidate the results of the field test, the accuracy and validity of each test sequence being related to the use of a constant light source of fixed size. The present invention solves the problem of variation of intensity and image size by providing for lateral movement along the optical path of the image forming apertured disc 44. As can be seen in FIGS. 2 and 3, the positioning of the disc is a function of the distance of the projection surface from the point of projection.

Image intensity is maintained as a constant by the use of the collimator 28 which provides a constant amount of light energy to the apertured disc 44 and through the aperture (45*a* in the exemplary embodiment) without regard to the positioning of the disc and aperture along the optical path.

Constant image size and sharp image focus are maintained by moving the image forming aperture 45*a* toward and away from the telescopic optical train (lenses 29/30). The tendency of a projection system using a fixed image is to provide a larger, out-of-focus projected image at greater distances. To overcome this tendency, the position of the projection surface, which is related to mirror positioning, serves to control the positioning of the apertured disc to and from the first lens 29 of telescopic optic. Thus, when the image is to be formed at a greater distance, the apertured disc is accordingly moved toward the first lens 29 of the telescopic optic, thereby maintaining image focus and size as projected by the telescope.

To maintain accuracy of interaction of the mirror positions and the positioning of the apertured disc, edge detectors (not shown) are added to the mirror positioning stepper motors to locate mirror position. Mirror positioning information is coordinated with apertured disc location information as developed by edge detector 68. A mathematical model for positioning the mirrors and the apertured objective, and a practical application of same are provided in the following paragraphs.

Positions on the hemisphere are given by two numbers, $\phi$ and $\theta$, as shown in FIG. 5a. FIG. 5b is a geometrical picture of the hemispheric surface. It is equivlent to a left handed coordinate system. It is also equivalent to a normal coordinate system where all values of $\theta$ are negative numbers as shown in FIG. 5c.

The most convenient system for describing image projector motion is one in which the z axis is not in the patient's line of sight but is coincident with the axis of rotation of the projection tower or bell crank 69 (FIG. 5d). It follows that there is a rotation of the coordinate system about the x axis. The position of an image in the new system expressed in terms of its position in the old system is given by the following transformation equation:

$$\begin{pmatrix} x' \\ y' \\ z' \end{pmatrix} = \begin{pmatrix} 1 & 0 & 0 \\ 0 & \cos\delta & +\sin\delta \\ 0 & -\sin\delta & \cos\delta \end{pmatrix} \begin{pmatrix} x \\ y \\ z \end{pmatrix}$$

Here, $\delta = 72.5°$; so: $\cos\delta = .3007058$, and $\sin\delta = .9537169$.

x, y, z are taken to normalized coordinates such that $x^2+y^2+z^2=1$. From this is can be seen that x, y and z are expressed in terms of $\theta$ and $\phi$ as follows:

$$x = \sin\phi \cos(-\theta) = \sin\phi \cos\theta,$$

$$y = \sin\phi \sin(-\theta) = -\sin\phi \sin\theta, \text{ and}$$

$$z = \cos\phi.$$

Applying the above transformation:

$$x' = x = \sin\phi \cos\theta,$$

$$y' = -\cos\delta \sin\phi \sin\theta + \cos\phi \sin\delta, \text{ and}$$

$$z' = +\sin\delta \sin\phi \sin\theta + \cos\phi \cos\delta.$$

From the equations:

$$x = \sin\phi \cos\theta,$$

$$y = \sin\phi \sin\theta, \text{ and}$$

$$z = \cos\phi$$

it can be seen that $\phi = \cos^{-1} z$ and $\theta = \tan^{-1} y/x$. The $\phi$ and $\theta$ values in the new system are:

$$\phi' = \cos^{-1} z' = \cos^{-1}[+\sin\delta \sin\phi \sin\theta + \cos\phi \cos\delta],$$

and $$\theta' = \tan^{-1}\frac{y'}{x'} = \tan^{-1}\left[\frac{-\cos\delta \sin\phi \sin\theta + \cos\phi \sin\delta}{\sin\phi \cos\theta}\right]$$

The geometry of the projector head is shown in FIG. 5e. For purposes of the example:

$$R = \text{radius of bowl} = 13'' = 33 \text{ cm.}$$

The light path is from (1) to (2) to (3) and to the image formed on the hemisphere at location $\phi'$, $\theta'$. A method is needed to calculate rotation of the projector elements, $\phi''$ and $\theta''$, when $\phi'$ and $\theta'$ are known. It can be seen from FIG. 5f that once $\phi''$ is given a fixed value, the value of $\phi'$ is also fixed no matter what value of $\theta''$ is chosen. That is, if:

$R = $ bowl radius, then:

$$r(\phi') = (a^2 + R^2 - 2aR \cos\phi')^{\frac{1}{2}}.$$

However light travels on a dog leg path (FIG. 5g). To know path length, the value of $p(\phi')$ must be known. Once $r(\phi')$ is known it can be seen that:

$$p(\phi') = (r(\phi')^2 - b^2)^{\frac{1}{2}}, \text{ and}$$

$$p(\phi') = (a^2 + R^2 - b^2 - 2aR \cos\phi')^{\frac{1}{2}}.$$

Therefore, if:

$a = 7.2'',$ $b = 1.38'',$ and $R = 13'',$ then:

$$p(\phi') = (218.94 - 187.2 \cos\phi')^{\frac{1}{2}}.$$

Now it is necessary to calculate $\phi''$ from a given value of $\phi'$. $\gamma$ is defined as shown in FIG. 5h so that:

$$R \cos\phi' = a + r(\phi') \cos\gamma, \text{ and}$$

$$R \cos\phi' - a = r(\phi') \cos\gamma.$$

Referring to FIG. 5i, a line, z'', parallel to z' is drawn through point (3). The angle between z'' and the line from (3) to the projected spot (5) is $\phi''$. The length of the line, (3)→(4), is $p(\phi') \cos\phi''$. The length of the line, (2)→(5), is $r(\phi') \cos\gamma'$. Because (3)→(4), and (2)→(5) are parallel and are projected from the same spot, they are of equal length. Therefore:

$$p(\phi') \cos\phi'' = r(\phi') \cos\gamma = R \cos\phi' - a.$$

Since $p(\phi')$; R, $\cos\phi'$ and "a" are known, $\phi''$ is given by:

$$\phi'' = \cos^{-1}\left(\frac{R\cos\phi' - a}{p(\phi')}\right) =$$

$$\cos^{-1}\left\{\frac{R\cos\phi' - a}{(a^2 + R^2 - b^2 - 2aR\cos\phi')^{\frac{1}{2}}}\right\}$$

where: $\cos\phi' = z' = \cos\phi \cos(72.5°) + \sin(72.5°) \sin\phi \sin\theta$.

The calculation of $\theta''$ is described next. For any fixed value of $\phi'$, the value of $\theta''$ is an angular displacement from some reference or starting position of the tower, picked so that the reference position coincides with the $\theta = 0°$ meridian. However, as $\phi'$ changes, the reference position also changes. This change must be accounted for in the calculations. To start, a reference position $\theta_o''$ for the case $\theta=0°$, $\phi=0°$ is defined. The reference is given by describing the direction of line (2)→(3) in $\phi'$, $\theta'$ space. When $\phi=0°=\theta$, $x'=0$, $y'=-\sin\delta$, and $z'=\cos\delta$. Therefore, $$\phi' = \delta, \text{ and}$$

$$\theta' = \tan^{-1}\frac{-\sin\delta}{0} = 90°.$$

In FIG. 5j, point (5) on axis z' is placed so that angle $<z'(5)S$ is a right angle. As discussed above, line (3)→(4) is parallel to line (2)→(5). Since angle $<(2)(3)(5)$ is a right angle and line (5)→(4) is parallel to line (2)→(3), angle $<(5)(4)(5)$ is also a right angle. The length of line (2)→(3) is known to be, b. Therefore, line (5)→(4) is also length, b. Because of this construction, line (5)→(S) is length $R \sin \phi'$. Thus, $R \sin \phi' \cos \theta_o''=b$, where $\theta_o''$ is angle $<S(5)(4)$, the direction of line (5)→(4) and the direction of line (2)→(3). Therefore:

$$\theta_o''(\phi') = \cos^{-1}\frac{b}{R \sin\phi'}.$$

For any other value of $\theta'$, $\theta''$ is defined by:

$$\theta'' = \theta' - \theta_o''(\phi'),$$

$$\theta'' = \theta' - \cos^{-1}\frac{b}{R \sin\phi'}.$$

Rotation about the $\phi''$ axis is accomplished by a linear stepper motor 93 and associated linkage 62 driving a bell crank 69 which rotates about the $\phi''$ axis. As FIG. 6a shows, $$m=(c^2+d^2-2cd \cos \beta)^{\frac{1}{2}}.$$

Since $d^2=c^2+e^2$; then $cd=c(c^2+e^2)^{\frac{1}{2}}$. Referring to FIG. 6b, there is used as a reference the position for which $\gamma=90°$. m and c can be directly measured when $\gamma=90°$ and used to compute $\beta_o$ where $\beta_o=\tan^{-1} m_o/c$.

The position for which $\gamma=90°$ is the midtravel position for the $\phi''$ stepper motor. It corresponds, by design, to a value of $\phi'$. However, $\phi'$ can also be measured on the hemisphere, which is the best way to proceed. Knowing $\phi'$, the next calculation is $\phi''$, where $$\phi'' = \cos^{-1}\left[\frac{R \cos\phi' - a}{(a^2 + R^2 - b^2 - 2aR\cos\phi')^{\frac{1}{2}}}\right] =$$

$$\cos'\left(\frac{R \cos\phi' - a}{\rho(\phi')}\right)$$

As can be seen in FIG. 6c, $\beta+\alpha+\phi''-\phi_o''=180°$, $\beta+\phi''=180°-\alpha+\phi_o''$.

Since $\alpha$ and $\phi_o''$ are constants, the sum $\beta+\phi''$ is also a constant. This means that any change in $\beta$ results in an equal change in magnitude in $\phi''$ and vice-versa. The signs of the changes are opposite. $\phi_o''$ can be set at any value as long as it is a constant. $\phi_o''$ is re-chosen as that value, which represents the value of $\phi''$ at $\gamma=90°$. Also $\beta_o$ is defined as the value of $\beta$ when $\gamma=90°$. Then $\beta=\beta_o+\Delta\beta$. But $\Delta\beta=-\Delta\phi''$ when $\Delta\phi''=\phi''-\phi_o''$. So $\beta=\beta_o+\phi_o''-\phi''$. Describing m as a function of $\beta$:

$$m=(c^2+d^2-2cd \cos \beta)^{\frac{1}{2}}=LS_{\phi''}+m_o.$$

$S_{\phi''}$ is the number of motor steps off the zero or initial position, L is the motor inches/step, $m_o$ is the value of m at the initial position.

$$S_{\phi''} = \frac{2(c^2 + e^2 - 2c(c^2 + e^2)^{\frac{1}{2}}\cos\beta)^{\frac{1}{2}} - m_o}{L}$$

For the $\theta''$ drive, the tower is belt driven by drive system 64 with a reduction of N. Therefore, since the reference position is taken as $\theta''=0$, $$S_{\theta''} = N\theta'' = N\left(\theta' - \cos^{-1}\frac{b}{R\sin\phi'}\right)$$

There is also aperture motor drive 73 to consider. Its function is to keep the image of the aperture on the hemispheric surface in focus. For purpose of illustration, the telescopic lens system 29, 30 will be taken to have telescopic power 2, although other powers would be workable. Then the optical system is such that a change of $\Delta x$ in aperture position results in a change of $4\Delta x$ in the position of the aperture image. The image of the aperture is measured from the objective lens 30. This lens is at a distance D from the hemispheric surface where: $D=\rho(\phi')=f$, where f will be taken as 1" in this example.

For some initial arrangement in which, D=the correct image distance, a change of $\Delta D$ must be accompanied by a change of $(\Delta D)/4$ in the aperture position to maintain focus. If $\Delta D=D-D_o$, and if $x_o$ is the x position corresponding to good focus at $D_o$; then, since $$\Delta x = (x - x_o) = \frac{\Delta D}{4} = \frac{D - D_o}{4}, x = \frac{(D - D_o)}{4} + x_o.$$

$$\text{Let } x_o = 0, \text{ then } x = \frac{\rho(\phi') - f - D_o}{4}.$$

If the motor rate=A(inches/step), then $$S_A = \frac{\rho(\phi')}{4A} - \left(\frac{f + D_o}{4A}\right)$$

If desired, it is possible to alter the value of $x_o$ for a given $D_o$ by interposing an additional lens 30a (shown in phantom) between lens 29 and lens 30. Such additional lens would be a mechanical expedient, allowing the travel path of the aperture disc to be shifted.

There are now developed the equations necessary to generate motor commands once values of $\theta$ and $\phi$ are chosen. The calculations are done most directly in the following order. Representative constants are used for illustrative purposes but are by no means the only values which can be used in practice.

(1) given: $\theta$ and $\phi$, calculate $\theta'$, $\cos\phi'$, $\sin\phi'$
constant $\delta = 72.5°$:
$\cos\phi' = \cos\phi \cos(72.5°) + \sin\theta \sin(72.5°) \sin\phi$ (a)
$\sin\phi' = (1 - \cos^2\phi')^{\frac{1}{2}}$ (b)

$$\theta' = \tan^{-1}\left[\frac{\sin 72.5°}{\tan\phi\cos\theta} - \cos 72.5°\tan\theta\right] \quad (c)$$

(2) Calculate $\rho(\phi')$ using $\cos\phi'$

-continued constants: $a = 7.2''$
$b = 1.38''$
$R = 13''$
$\rho(\phi') = (a^2 + R^2 - b^2 - 2aR\cos\phi')^{\frac{1}{2}}$
$\rho(\phi') = (218.94 - 187.2\cos\phi')^{\frac{1}{2}}$ (3) Calculate $\theta''$ using $\cos\phi'$ and $\rho(\phi')$
constants: $R = 13''$
$a = 7.2''$ $$\phi'' = \cos^{-1}\left(\frac{13\cos\phi' - 7.2}{\rho(\phi')}\right)$$

(4) Calculate $\beta$ using $\phi''$
constants: $\phi_0'' = 94.7°$
$m_o = 6''$
$c = .89''$ $$\beta_o = \tan^{-1}\frac{m_o}{c} = 81.6°$$

$\beta = 176.3° - \phi''$ (5) Calculate $m$ using $\beta$
constants: $c = .89''$
$e = 6''$
$m = (37.58 - 10.8\cos\beta)^{\frac{1}{2}}$ (6) Calculate motor steps using $\theta'$, $\sin\phi'$, $m$ and $\rho(\phi')$
constants: $n = 2$ step/degree
$L = .004''$/step
$A = .03063''$/step
$b = 1.38''$
$R = 13''$
$m_o = 6''$
$f + D_o = \rho_o(\phi') = 11.34''$ $$S_{\phi''} = \frac{m - m_o}{L} = 250(m - 6)$$

$$S_{\phi''} = 2\left(\theta' - \cos^{-1}\left(\frac{.106}{\sin\phi'}\right)\right)$$

$$S_A = 8.16(\rho(\phi') - 11.34)$$

The edge detector and stepper motor type servo is well known in the art. Basically, the edge detector defines a reference or initial location for the servo component, such as the apertured disc. The stepper motor moves a control component a predictable distance for each drive pulse it receives. Thus, if three pulses of a first polarity are supplied to the step motor when the controlled component is at the edge detector, two things are known: the number of pulses of opposite polarity required to return the component to the edge detector position and the distance the component has been moved from the edge detector.

In some embodiments of the invention, a photocell and lens 63 is also added, as discussed above, for sampling background intensity and projected image intensity. The photocell determines the Weber fraction or contrast, and fine adjusts the intensity of the image, if necessary, to maintain constant image intensity. The Weber fraction is defined as follows:

$W = [(\Delta L)/L]$ where:
L = background luminance; and
$\Delta L = L_s - L_b$ (luminance of source minus background luminance).

To insure accurate field testing, the patient's eye must remain constantly fixated on a reference location, such as a center portion of the hemisphere 20. To maintain such alignment, it is desirable to monitor the positioning of the patient's eye, as well as to provide a fixation point for the patient. FIG. 1 shows a view finding system 23 and an observer's eye 13. FIG. 4 shows the view finding system 23 in detail. A peep hole 15 is provided at a center portion of the hemisphere 20. The peep hole should be small and should be positioned such that a patient's eye may easily be aligned with it. Because the surface of the tester is maintained in relative darkness to allow easy perception of the projected images by the patient, very little light is reflected from the patient's eye. Thus, a viewing and centering system must efficiently use the available light.

The present invention comprises a mirror 76 which gathers light passing through peep hole 15 and reflects said light to a first lens 77. The positioning and refractive power of the first lens 77 is such that it creates, in conjunction with second lens 78, an image of peep hole 15 in the plane of and centered in the pupil of the examiner's eye 13. In addition, lens 77 and 78 create a magnification system such that the image created of the peep hole 13 is the same size as or a little smaller than the pupil of the examiners eye 13. Therefore, all the light passing through peep hole 13 into first lens 77 passes into the examiner's eye with little loss. Indeed, it is as though the examiner physically pressed his eye against peep hole 13 and viewed the patient's eye.

First lens 77 also creates a real image of the patient's eye in the space between lens 77 and the second lens 78. Second lens 78 is positioned so that this real image falls at approximately one focal length from it. In addition reticle 79 is placed in the plane of this real image so that both it and the real image can easily be viewed simultaneously in focus by the examiner. Reticle 79 is provided with cross hair 80 to aid in centering the patient's eye and with a graduated scale by which the size of the patient's pupil may be measured.

To fixate the patient's eye a first light source such as LED 82 is provided. The LED 82 is centered on mirror 76 such that the patient most clearly perceives the light source when his eye is in proper alignment for field testing.

To add further precision to the fixation system a second light source, such as LED 81, may be added at lens 77. Thus, two points of fixation are provided such that when the eye is aligned, the light sources 81/82 converge. Such a system assures a high degree of accuracy when aligning a patient's eye for field testing. It will be appreciated that other light sources, such as neon lights, lamps, etc. may be used in place of the LED.

The present invention provides a field tester including a off-center objection system that does not interfere with alignment of a patient's eye within a hemispheric projection surface of said field tester. By use of the above described optical train a projected image, selected according to predetermined criteria, is maintained in a constant size and intensity on the hemispheric projection surface during a testing sequence. As a result, excellent accuracy is obtained in field testing. To further enhance the reliability and accuracy of tests performed with this device, a wide angle viewing device has also been described for aligning the patient's eye by observation or by patient fixation.

It will be appreciated that modifications and variations may be made to the invention as described without departing from the scope and spirit of the invention as claimed. For example, the optical train may be further folded by the inclusion of additional mirrors, positioning of the apertured disc and the mirrors may be accomplished by servo systems other than those described above or by manual adjustment, etc. Therefore, the scope of the invention should be limited only by the breadth of the claims.

We claim:

1. An off-center projection system for a hemispheric projection surface, comprising:
   a light source;
   means for collimating light from said light source;
   a movable apertured member within a path of said collimated light;
   telescopic optics within said collimated light path for projecting an image of said aperture onto said projection surface; and
   means for moving said apertured member wherein said projected image size and intensity remains constant, according to selected image criteria, despite a constantly changing distance between a point of projection and a point on said projection surface where said image is formed.

2. The projection system of claim 1, said telescopic optics further comprising:
   a first mirror pivotable about a first axis for projecting said image onto said projection surface; and
   means for pivoting said mirror.

3. The projection system of claim 2, said telescopic optics further comprising:
   a second mirror about a second axis, orthogonal to said first mirror pivot axis for projecting said image onto said projection surface; and
   means for pivoting said second mirror.

4. The projection system of claim 3, said collimating means further comprising:
   a first condensing lens proximate to said light source and located on one side of said apertured member.

5. The projection system of claim 4, further comprising:
   an optical stop along said light path.

6. A field tester, including an off-center projection system for forming an image having constant size and brightness over varying distances, according to selected image criteria, onto a hemispheric projection surface, comprising:
   a light source;
   a condenser collimator for supplying constant light energy from said light source over a collimated light path;
   an apertured member movable along and within said collimated light path, said member receiving light of substantially constant intensity from said collimator;
   means for moving said apertured member selected distances to and from said light source along said light path; and
   a constant magnification telescope within said collimated light path including an optical train for projecting an image of said member's aperture onto said projection surface, said optical train including at least a first lens at an image reception point and a second lens at an image projection point.

7. The field tester of claim 6, said apertured member further comprising:
   a plurality of individually selectable apertures having differing diameters.

8. The field tester of claim 6, further comprising:
   a neutral density filter having a selectively variable density and interposed within said optical train.

9. The field tester of claim 6, further comprising:
   a color filter wheel having selectable filter elements of varying colors and interposed within said optical train.

10. The field tester of claim 6, further comprising:
    light detecting means for receiving light from said hemispheric projection surface, said light being indicative of intensity on said projection surface and indicative of intensity of said projected image, said light detecting means including means for effecting changes in said image intensity to maintain a constant image intensity during a test sequence.

11. The field tester of claim 6, further comprising:
    a first mirror, within said telescope and pivotable about a first axis, for folding said optical train;
    a second mirror, within said telescope and pivotable about a second axis, orthogonal to said first mirror pivot axis, for projecting said image through said second lens and onto said projection surface; and
    means for pivoting said first and second mirror wherein said telescopic optics may project an image onto said projection surface at any selected location thereon.

12. The field tester of claim 11, further comprising:
    an optical stop within said optical train.

13. The field tester of claim 11, further comprising:
    servo means, coupled to said movable apertured member and to said first and second pivotal mirrors, for maintaining conjugate distance of said member's aperture from said telescope optics first lens as a function of distance from said point of projection to said projection surface.

14. The field tester of claim 13, said servo means further comprising:
    first stepper motor means for moving said apertured member along said light path to and from said first telescope lens;
    second stepper motor means for pivoting said first mirror about said first axis;
    third stepper motor means for pivoting said second mirror about said second axis; and
    each stepper motor including edge detector means for sensing the position of each stepper motor relative to an initial motor position.

15. Apparatus for testing field of vision of a patient's eye comprising:
    a hemispheric projection surface including a peep hole formed through a center portion thereof;
    a source of collimated light;
    telescopic optics within a path of said collimated light for projecting a test image onto said projection surface from a point of projection off-center of said projection surface;
    a movable apertured member within said collimated light path, said member interposed between said light source and said telescopic optics to form a test image of said aperture for projection by said telescopic optics;
    means for moving said apertured member wherein said projected test image size and intensity remain constant according to selected image criteria although there is a varying distance between the point of projection and each point on said projection surface where said test image is formed;
    a first lens, positioned at a fixed distance from said peep hole on a convex side of said hemispheric projection surface, for forming an image of said peep hole onto an examiner's eye; and a second lens, positioned a fixed distance from said first lens, for viewing said peep hole image to center the patient's eye.

16. A field tester, comprising:

an off-center projection system for forming an image having constant size and brightness according to selected image criteria, over varying distances onto a hemispheric projection surface, including:
  (a) a light source;
  (b) a condenser collimator for supplying constant light energy from said light source over a collimated light path;
  (c) an apertured disc, movable along and within said collimated light path, said disc receiving light of substantially constant intensity from said condenser collimator;
  (d) means for moving said apertured disc selected distances to and from said light source along said light path; and
  (e) a constant magnification telescope within said collimated light path, including an optical train projecting an image of said disc's aperture onto said projection surface, said optical train including a first lens located at an image reception point and a second lens located at an image projection point; and a wide angle viewing system for centering a patient's eye during field of vision testing, including:
  (a) a peep hole formed through a center portion of said hemispheric projection surface;
  (b) a first lens positioned at a fixed distance from said peep hole on a convex side of said hemispheric surface for forming an image of said peep hole onto an examiner's eye; and
  (c) a second lens positioned a fixed distance from said first lens for viewing said peep hole image.

17. A method for forming an image having constant size and and brightness according to selected image criteria over varying distances onto a hemispheric projection surface of a field tester, comprising:

collimating a source of light to supply constant light energy from said light source over a collimated light path;

forming an image to be projected on said hemispheric projection surface with a movable apertured member;

projecting said image onto said projection surface with a constant magnification telescope; and maintaining said projected image at a constant size and intensity according to selected image criteria on said projection surface by moving said apertured member to and from said constant magnification telescope in response to change in distance from a telescope point of projection to said hemispheric projection surface.

* * * * *